United States Patent [19]

Powers, Jr.

[11] 4,081,991
[45] Apr. 4, 1978

[54] APPARATUS FOR PRESSURE TESTING FRANGIBLE CONTAINERS

[75] Inventor: Whitney S. Powers, Jr., Pine City, N.Y.

[73] Assignee: Powers Manufacturing, Inc., Elmira, N.Y.

[21] Appl. No.: 712,991

[22] Filed: Aug. 9, 1976

[51] Int. Cl.² .............................................. G01M 3/04
[52] U.S. Cl. .......................................... 73/41; 73/45.2; 198/339
[58] Field of Search ................ 73/37, 45.1, 45.4, 45.2, 73/41, 49.2, 49.8; 198/339

[56] References Cited

U.S. PATENT DOCUMENTS

| | | | |
|---|---|---|---|
| 2,084,653 | 6/1937 | Preston | 73/45.1 X |
| 2,314,310 | 3/1943 | Jackson et al. | 73/41 |
| 3,388,588 | 6/1968 | Vincenot | 73/49.8 X |
| 3,433,079 | 3/1969 | Wilson | 73/49.8 |
| 3,496,761 | 2/1970 | Powers, Jr. | 73/45.2 |
| 3,683,677 | 8/1972 | Harris | 73/49.2 |
| 3,827,284 | 8/1974 | Armstrong et al. | 73/45.1 |
| 3,837,215 | 9/1974 | Massage | 73/45.4 |
| 3,894,424 | 7/1975 | Taylor et al. | 73/49.2 |

Primary Examiner—Daniel M. Yasich
Attorney, Agent, or Firm—Seidel, Gonda & Goldhammer

[57] ABSTRACT

Apparatus for pressure testing frangible containers includes a carriage quided for horizontal reciprocation while supporting and guiding a pressure conduit mounted for vertical reciprocation. A pair of jaws are provided for embracing and supporting a container from above as the container is hydrostatically subjected to internal pressure.

10 Claims, 9 Drawing Figures

APPARATUS FOR PRESSURE TESTING FRANGIBLE CONTAINERS

BACKGROUND OF THE INVENTION

The invention relates generally to internal pressurization of frangible containers with a liquid such as water. A number of hydrostatic pressure testing devices have been proposed heretofore. For example, see U.S. Pat. No. 2,314,310 and U.S. Pat. No. 3,387,704.

The substantial growth in the usage of carbonated beverage and malt beverage containers has required significant increases in the rate of manufacture of containers in the glass container industry. Many more containers must be pressure tested to ensure quality. The invention relates to an automatic apparatus for performing the pressure tests and of recording the resultant data.

SUMMARY OF INVENTION

The present invention is directed to apparatus for pressure testing of frangible containers such as containers made of glass. The apparatus includes a conveyor for moving containers to the test station at which is located a carriage guided for horizontal reciprocation parallel to the conveyor. The carriage is disposed above the conveyor and supports a pressure conduit mounted for movement with the carriage. A means is provided for guiding movement of the pressure conduit in a vertical direction while the carriage and the conduit are moving horizontally.

A pair of jaws are supported adjacent the lower end of the pressure conduit. A means is provided on the carriage for moving the jaws between open and closed positions as a function of the elevation of the jaws relative to said conveyor. A head is provided on the lower end of said conduit for sealing contact with the open end of a container to be tested and for introducing a liquid under pressure from said conduit into the container while the container is supported from above by said jaws. A supply conduit is connected to said pressure conduit for introducing water under pressure into said pressure conduit.

In accordance with the present invention, the frangible container is suspended from above by jaws when subjected to high hydrostatic pressures such as 200 psi. When a container is subjected to the high hydrostatic pressure, more reliable results are obtained when the frangible container is suspended from above as compared with a container supported from below by a conveyor or some other support surface. Another refinement of the apparatus of the present invention is the provision of means for selectively resisting upward movement of the pressure conduit when a container supported by the jaws is subjected to the high hydrostatic pressure to thereby assure that the reaction force of the hydrostatic liquid does not cause a separation between the pressure conduit head and the open end of the container. The last-mentioned means is independent of the means which causes vertical reciprocation of the pressure conduit. Other advantages and features of the apparatus of the present invention will be apparent from the following description.

For the purpose of illustrating the invention, there is shown in the drawings a form which is presently preferred; it being understood, however, that this invention is not limited to the precise arrangements and instrumentalities shown.

Referring to the drawing in detail, wherein like numerals indicate like elements, there is shown apparatus in accordance with the present invention designated generally as 10.

Figure 1:
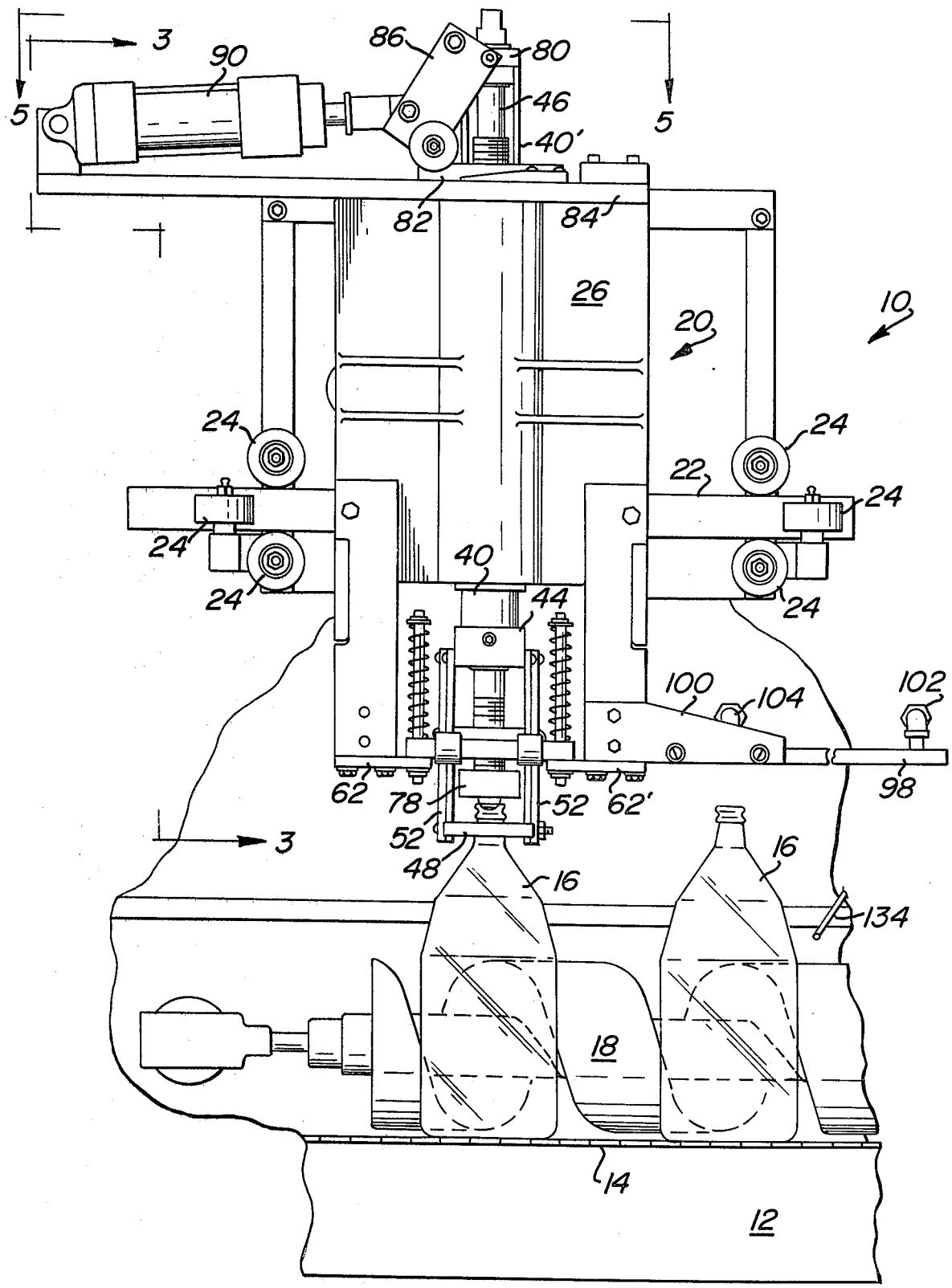
FIG. 1 is a front elevation view of apparatus in accordance with the present invention.

The apparatus 10 includes a stationary frame 12 which supports an endless horizontally disposed conveyor 14. Frangible containers 16 made from a material such as glass are supported from below and moved by the conveyor 14 at a rate determined by the screw conveyor 18. Screw conveyor 18 maintains the containers 16 at a predetermined distance apart from one another. See FIG. 1.

A carriage 20 is supported from the stationary frame for horizontal reciprocation parallel to the direction of movement of the container 16. The carriage 20 includes a horizontally disposed guide 22 secured thereto in any convenient manner such as by bolts. A plurality of idler rollers 24 are supported by the stationary frame. Each of the idler rollers 24 contacts one surface of the guide 22 which is rectangular in cross section. It will be noted that idler rollers are provided adjacent each end of the guide 22 on opposite sides of the carriage housing 26.

Figure 2:
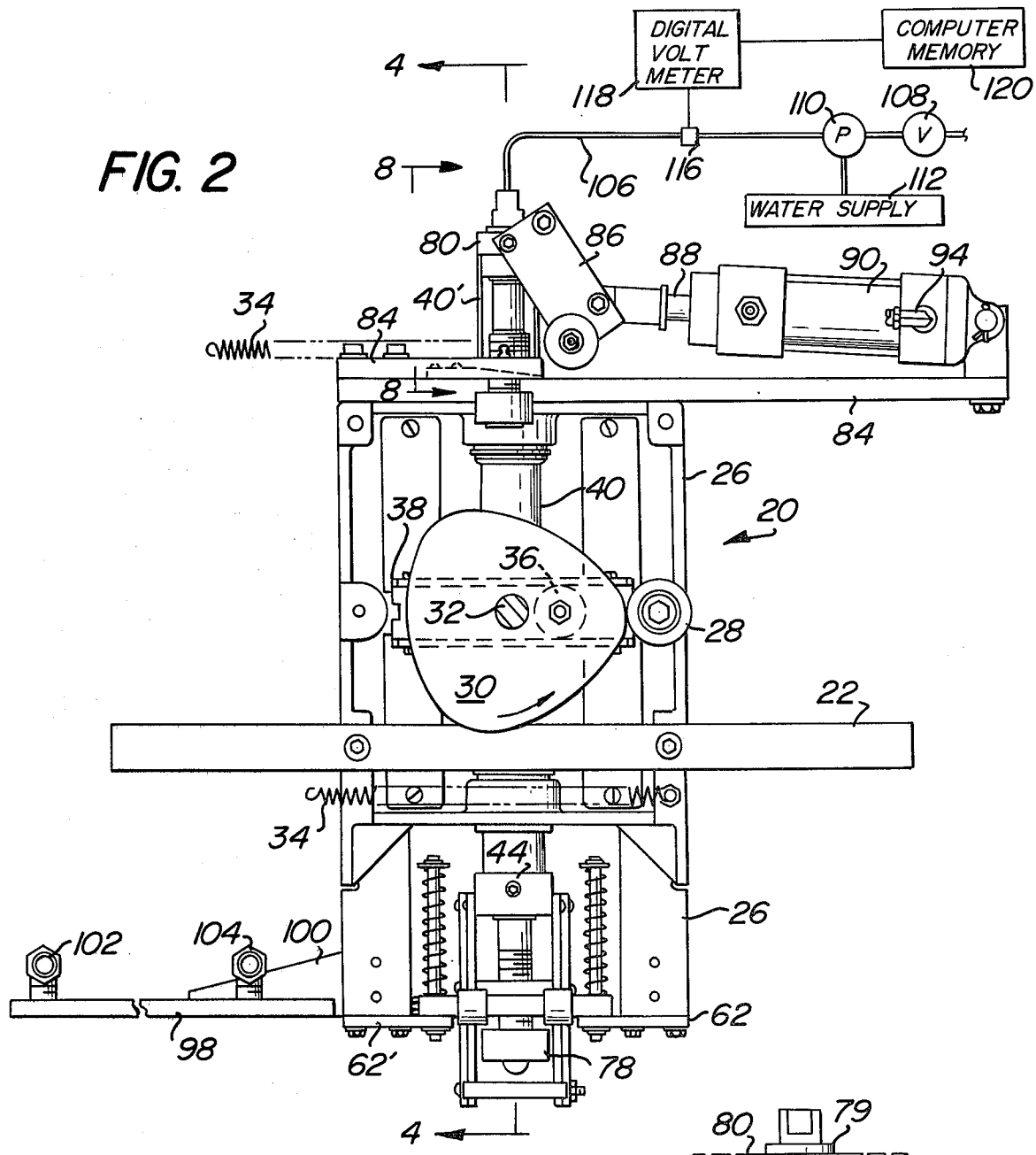
FIG. 2 is a rear elevation view of apparatus in accordance with the present invention.
Figure 8:
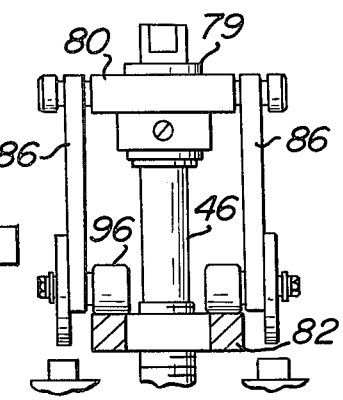
FIG. 8 is a sectional view taken along the line 8—8 in FIG. 2.

A cam follower 28 is supported by the carriage housing 26. See FIG. 2. Follower 28 is in contact with the periphery of a cam 30 supported by shaft 32 rotatably driven by a motor not shown. As the cam 30 rotates due to rotation of shaft 32, the contact between the cam 30 and follower 28 causes the carriage 20 to reciprocate in one direction with linear motion corresponding to the speed of conyor 18. A plurality of springs 34 have one end connected to a stationary part of the frame and their other end connected to the carriage housing 26. The springs 34 cause the carriage to return in the opposite direction and maintain contact between the cam 30 and the follower 28.

The cam 30 rotatably supports the follower 36 which extends into a yoke 38. Yoke 38 is connected to a hollow shaft 40. See FIG. 4. While the carriage 20 is reciprocating, the follower 36 cooperates with the yoke 38 to cause the hollow shaft 40 to move in a vertical direction. Yoke 38 may be connected to the hollow shaft 40 in any convenient manner.

Figure 4:
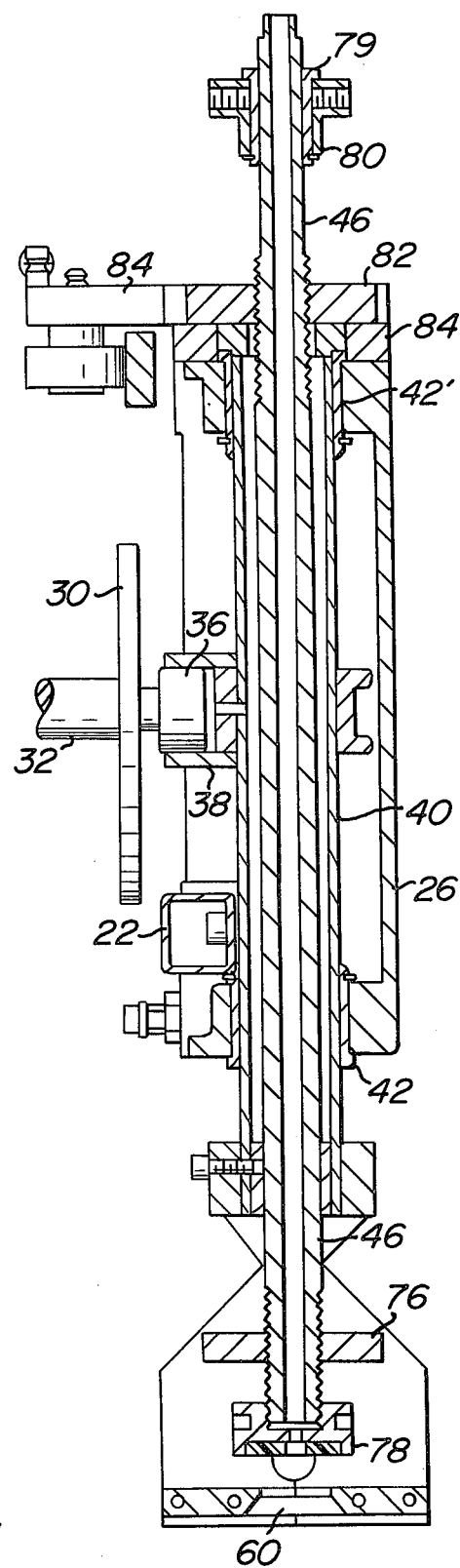
FIG. 4 is a sectional view taken along the line 4—4 in FIG. 2.

The hollow shaft 40 is guided for vertical reciprocation by a lower bushing 42 and an upper bushing 42' on the carriage housing 26. See FIG. 4. A fitting 44 on the lower end of the hollow shaft 40 is releasably connected to a guide bushing surrounding pressure conduit 46 in any convenient manner such as by a set screw. As shown in FIG. 4, the pressure conduit 46 is surrounded by the hollow shaft 40. Shaft 40 and conduit 46 are not directly connected together, but each are guided for vertical movement. Vertical movement of conduit 46 is only about 1 inch.

A pair of cooperating jaws 48 and 50 are provided adjacent the lower end of the shaft 40 for movement therewith in a manner so that the open and closed disposition of the jaws is a function of the elevation of said shaft 40. The jaws 48, 50 are connected to the fitting 44. See FIG. 6. Each jaw has a soft plastic semi-circular insert as its container-engaging surface.

Figure 3:
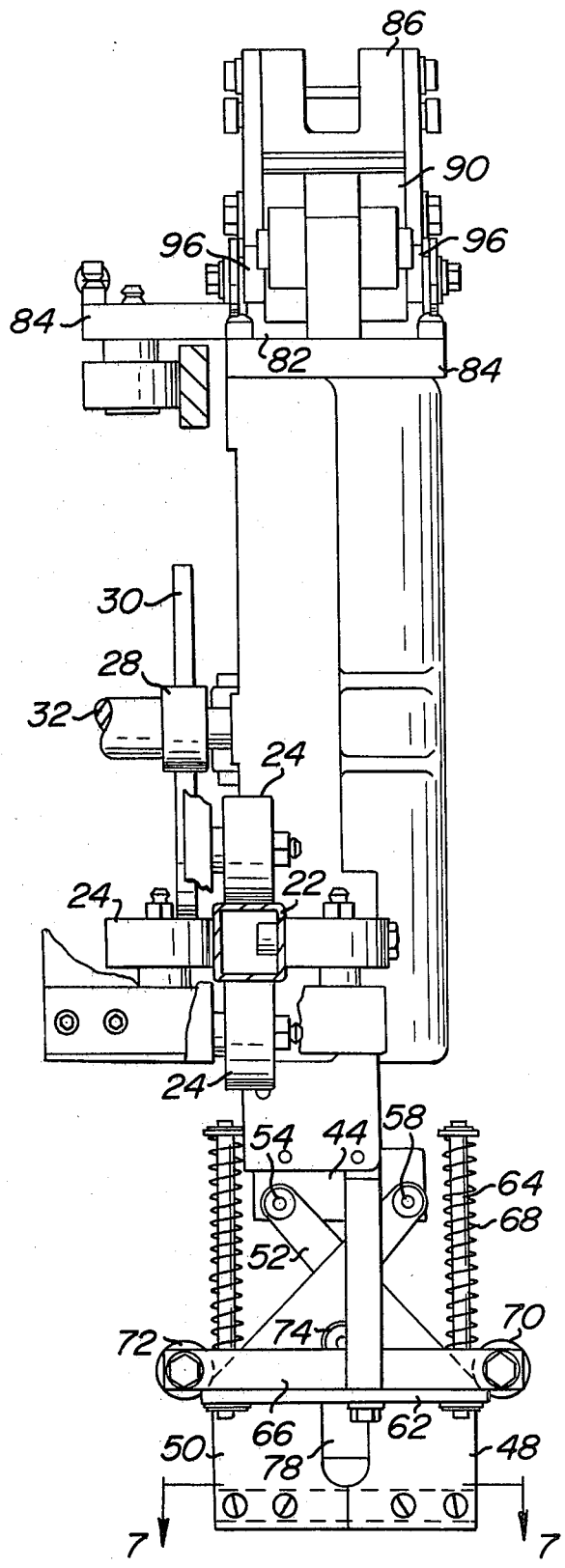
FIG. 3 is a view as seen along the line 3—3 in FIG. 1.
Figure 6:
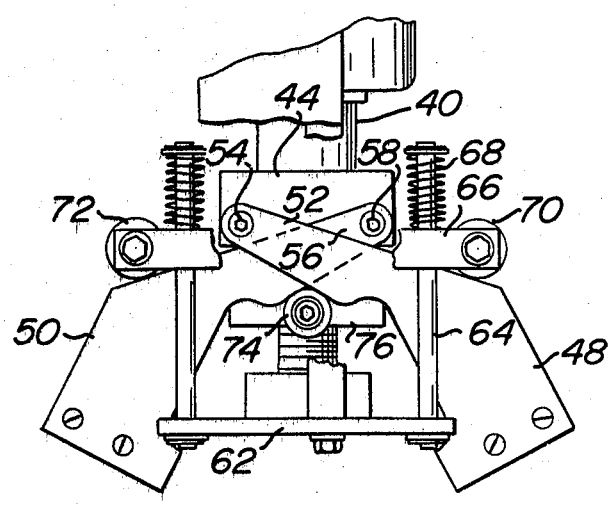
FIG. 6 is an enlarged detail view of the jaws as shown in FIG. 3 but illustrated in an open disposition.
Figure 7:
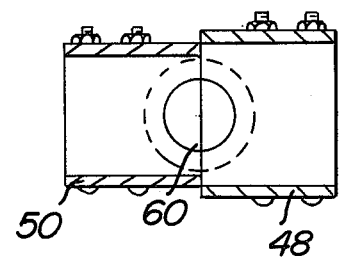
FIG. 7 is a sectional view taken along the line 7—7 in FIG. 3.

As shown more clearly in FIGS. 1 and 6, the jaw 48 has a pair of links 52 extending upwardly therefrom on opposite sides thereof. The upper end of each link 52 is pivotably connected to the fitting 44 by a pivot pin 54. Jaw 50 is similarly provided with a pair of upwardly extending links 56 pivotably connected to the fitting 44 by pivot pins 58. Each of the jaws 48, 50 is provided with a semi-circular notch on its inner periphery so that the notches in the closed dispositions of the jaw provide a circular opening 60 for embracing the neck of the container 16. See FIG. 7. A pair of support members 62 and 62' are attached by upright braces to the carriage 20. See FIGS. 1–3. A plurality of posts 64, such as two in number, are provided on the upper surface of each of the support members 62, 62'. An annular lock member 66 is provided with holes adjacent its periphery through which the posts 64 extend. The posts 64 guide the lock member 66 for vertical movement. A spring 68 surrounds each of the posts 64 and biases the lock member 66 downwardly into contact with the upper surface of the support members 62, 62'. See FIGS. 3 and 6.

The upper edges of the links 52, 56 are straight. The upper edges of the links 52 contact rollers 70 on the lock member 66. The upper edges on the links 56 contact rollers 72 on the lock member 66. Hence, as the links pivot outwardly, they cause the lock member 66 to move upwardly against the pressure of the springs 68. When the jaws 48, 50 are in their closed position, the springs 68 bias the lock member 66 against the support members 62, 62'.

The lower edge of each set of links 52, 56 define a cam surface for cooperation with a discrete jaw opener 74. See FIGS. 3 and 6. The jaw openers 74 are mounted on support 76 which adjustably connects to the pressure conduit 46. Support 76 is smaller than the central hole in member 66 to prevent interference contact. When the shaft 40 is descending with the jaws 48, 50 embracing the neck of a container 16, the links 52, 56 contact the jaw openers 74 which cause the jaws to pivot to the position shown in FIG. 6. The elevation at which the jaws 48, 50 open is selectively adjustable by way of the threaded connection between support 76 and the pressure conduit 46.

Referring to FIGS. 1 and 4, a guide bushing 79 for conduit 46 is supported by a bracket 80. The bracket 80 is supported by an extension 40' on shaft 40. A mounting plate 82 is threadedly secured to the outer periphery of the pressure conduit 46 at an elevation above the elevation of carriage top plate 84. The upper end of a clevis 86 is pivotably connected to the bracket 80. The lower end of the clevis 86 is pivotably connected to one end of a piston rod 88. Piston rod 88 extends from one end of an air cylinder 90. The other end of cylinder 90 is pivotably connected to the top plate 84 which is fixed to carriage 20.

Figure 5:
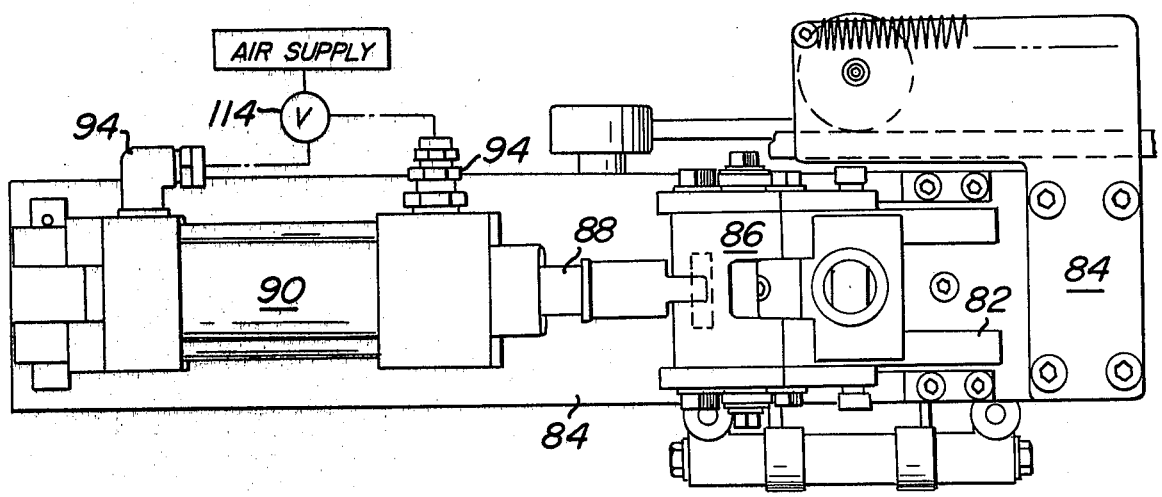
FIG. 5 is a top plan view of the apparatus as illustrated in FIG. 1.

The clevis 86 supports a pair of rollers 96 between the legs of the clevis. See FIGS. 1 and 5. The rollers 96 are adapted to contact the plate 82 and impart a downward force on the pressure conduit 46. The plate 82 is generally H-shaped in plan view with its cross bar being the portion connected to the pressure conduit 46. In the lowermost position of conduit 46, the lower surface of plate 82 contacts the upper surface of plate 84. The cylinder 90 is provided with inlet fittings 94 for introducing air under pressure to control the position of the piston rod 88.

A plate 98 is supported by the lower end of the carriage housing 26 and projects upstream with respect to the conveyor 12. See FIG. 1. The plate 98 is supported from the carriage housing 26 by brackets 100. Plate 98 supports nozzles 102 and 104 which are adapted to direct a stream of water downwardly toward the open end of the containers 16. The distance between the nozzles 102 and 104 corresponds to the distance between the nozzle 104 and the pressure conduit 46 which in turn corresponds to the pitch of conveyor 18.

The upper end of the pressure conduit 46 is releasably connected to a flexible supply conduit 106. Conduit 106 is connected to a water supply 112 by way of pump 110. See FIG. 2. Valve 108 is a cam operated air valve which controls the flow of air to a pneumatic booster on pump 110. Valve 108 is preferably connected into a control circuit with a solenoid operated valve 114 of the supply and exhaust type. When valve 108 is open, valve 114 is open and pressurized air is being directed into cylinder 90 to extend the piston rod 88. When valve 108 is closed, valve 114 is in a position so that pressurized air is introduced into the cylinder 90 to retract the piston rod 88 to the position shown in FIG. 2. Valves 108 and 114 are opened and closed by cam controlled switches, not shown, on shaft 32.

A pressure transducer 116 is connected to a portion of conduit 106 to monitor the pressure in said conduit. The pressure transducer 116 is connected to a control device for monitoring the pressure in conduit 106 and generating a signal indicative of a sharp drop in pressure responsive to a container 16 breaking under the hydrostatic pressure. A typical control device 118 would be a digital voltmeter. The control device 118 is coupled to a computer memory 120 and transmits a signal indicative of the highest pressure sustained by each container.

The computer memory 120 is coupled to other circuitry not shown for receiving a signal indicative of a particular mold or other origin of the specific container being tested so that control information may be ascertained that a container 16 from a particular molding machine was defective and that additional containers from that molding machine in accordance with statistical quality control data should be tested. The control device 118 is preferably also connected to an ejector not shown, which may be triggered by device 118 for ejecting broken glass off the conveyor 12 when a container being tested fails. Device 118 will also initiate diverting additional containers from the same source off the production line until acceptable testing of containers from that source is achieved.

Figure 9:
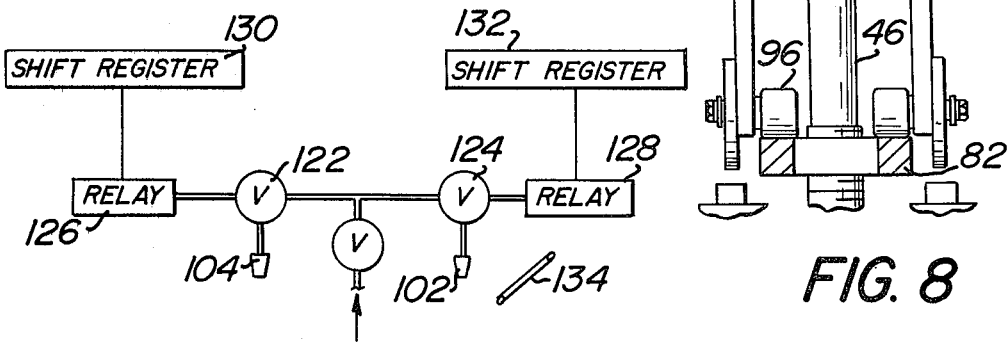
FIG. 9 is a schematic illustration of filling nozzles and associated controls.

Referring to FIG. 9, a nozzle 102 is supplied by a conduit containing a solenoid operated valve 124. Nozzle 104 is connected to a conduit containing a solenoid operated valve 122. The nozzles are supplied by a common supply conduit of water under pressure. Valve 122 is controlled by a relay 126 connected to a shift register 130. Valve 124 is controlled by relay 122 connected to a shift register 132. The shift register 132 is connected to a switch having an activating lever 134 adapted to project into the path of movement of the container 16 for contact therewith. The shift registers 130, 132 track the container 16 and automatically trigger operation of the valves 122, 124 so that the containers 16 are filled with water by nozzles 102, 104.

The following is a summary of the sequence of events beginning at the start position of the reciprocation of carriage 20. Jaws 48, 50 close around the neck of container 16 as shaft 40 moves upwardly due to cooperation of elements 36, 38 and expansion of springs 68. Carriage 20 moves horizontally while container 16 is suspended by the jaws. Cylinder 90 is activated to offset the reaction force on conduit 46 which transmits high pressure liquid to container 16 which is now being pressure tested. Cylinder 90 is then deactivated. Shaft 40 descends at the end of the carriage stroke. Jaws 48, 50 contact openers 74 as they descend and open so as to deposit container 16 back onto the conveyor. Carriage 20 returns to start position.

The operation of apparatus 10 will be clear to those skilled in the art in view of the above description and attached drawings. Hence, only a general sequence of steps is deemed necessary.

A container 16, filled with water and while it is controlled by screw conveyor 18, is embraced by jaws 48, 50. The jaws 48, 50 are locked closed to withstand the sealing force by lock member 66 unless the container neck is deformed and oval. If the neck is not round, the jaws will not close, the sealing force will not be resisted, no pressure will be developed, and the container will be read as defective. If the container neck is round, the hollow shaft 40 is then moved upwardly by follower 36 which causes jaws 48, 50 to lift the container 16 off the conveyor 14 and into contact with head 78. At the same time, the carriage 20 begins to move horizontally at the same linear speed that container 16 was moved by conveyor 18.

As the carriage 20 is moving horizontally from right to left in FIG. 1, cylinder 90 is activated. A downward pressure is exerted on conduit 46 by contact between rollers 96 and plate 82. Also, valve 108 opens so that a liquid, such as water under pressure, is communicated to the container 16 by way of conduits 46 and 106 for a short period of time. Then valve 108 is closed and piston rod 88 is retracted. At this point in time, the carriage 20 has reached the end of its horizontal stroke. The conduit 40 is then caused to descend by follower 36.

As conduit 40 descends, the container 16 is returned to the conveyor 14 and jaws 48, 50 immediately open. Opening of the jaws 48, 50 is attained by contact between jaw openers 74 and the lower edges of the links 52, 56 as the latter descend. See FIG. 6. Springs 68 are compressed as the jaws 48, 50 open.

The carriage 20 then reciprocates horizontally to its starting position and the jaws 48, 50 remain in their open position as shown in FIG. 6. When carriage 20 reaches its initial starting position for repeat of the sequence on the next container 16, hollow conduit 40 is moved upwardly. As the springs 68 expand, they cause the jaws 48, 50 to embrace the next container 16. This sequence is then repeated.

Each container 16 trips lever 134 so that the containers 16 are automatically filled with water as they pass beneath nozzles 102, 104. Such movement of the containers is tracked by the shift registers 130, 132. Meter 118 displays the pressure to which the containers were subjected and transmits a signal indicative of pressure to the computer memory 120. If the last-mentioned signal is non-uniform, indicative of a container having broken due to the pressure it was subjected to, or a pre-established pressure level was not achieved, the computer memory 120 may call for additional containers of the same type until acceptable tests on that type of container are achieved and/or will store such information for quality control purposes.

The present invention may be embodied in other specific forms without departing from the spirit or essential attributes thereof and, accordingly, reference should be made to the appended claims, rather than to the foregoing specification as indicating the scope of the invention it is claimed:

1. Apparatus for pressure testing frangible containers comprising a conveyor for moving containers along a horizontal path, a carriage guided for horizontal reciprocation parallel to said path, a vertically disposed pressure conduit supported by said carriage for horizontal reciprocation with said carriage, means on said carriage for causing movement of said conduit in a vertical direction while the carriage is moving horizontally, means including a pair of jaws supported by said carriage adjacent the lower end of said conduit for lifting a container off said conveyor and supporting the container during such horizontal reciprocation and for returning the container to said conveyor at the end of such horizontal reciprocation, means on said carriage for moving said jaws between open and closed positions as a function of the elevation of said jaws with respect to said conveyor with the jaws being open at the beginning and end of said reciprocatory movement of said carriage and with the jaws remaining open on the return stroke of said carriage, a head on the lower end of said conduit for sealing contact with the open end of the container to be tested and for introducing a liquid under pressure from said conduit into a container to be tested while the container is supported from above by said jaws, a supply conduit connected to said pressure conduit for introducing the liquid under pressure thereinto only while the container is supported from above by said jaws, and a selectively operable means on said carriage for preventing upward movement of said pressure conduit when a liquid is being introduced into a container by said pressure conduit, thereby opposing any upward reaction force from the pressurized liquid.

2. Apparatus in accordance with claim 1 including nozzle means movable with the carriage for filling containers with a liquid at a location upstream from the head on the lower end of said pressure conduit.

3. Apparatus in accordance with claim 2 including valve means associated with said nozzle means, said valve means being coupled to and operated by a shift register means adapted to track the position of a moving container on said conveyor.

4. Apparatus in accordance with claim 1 including a pressure transducer for detecting the pressure of liquid in said pressure conduit, means coupled to said transducer for transmitting a signal indicative of said pressure and any sudden drops of the pressure.

5. Apparatus in accordance with claim 1 wherein said jaws are each suspended from above by a pair of links, each link on each jaw cooperating with a mating link on the other jaw in a scissor-like arrangement, each link having a cam surface on its upper edge, a lock member biased downwardly, a cam surface on said links for moving said lock member upwardly as said jaws move to an open position, the bias on said lock member being arranged to move the jaws to a closed position.

6. Apparatus in accordance with claim 5 including means for adjusting the elevation upper ends of the jaw links with respect to a means for opening the jaws.

7. Apparatus in accordance with claim 1 wherein said selectively operable means includes a toggle link pivotably connected at one end to said pressure conduit and a power cylinder having a piston rod pivotably connected to the other end of said link.

8. Apparatus for pressure testing frangible containers comprising a conveyor for moving containers along a horizontal path, a carriage guided for horizontal reciprocation parallel to said path between a starting point to an ending point, a vertically disposed pressure conduit mounted on said carriage for horizontal reciprocation therewith, means including a pair of jaws supported by said carriage adjacent the lower end of said conduit for lifting a container off said conveyor at said starting point and for returning it to the conveyor at said ending point, means on said carriage for moving said jaws between open and closed positions as a function of the elevation of said jaws with respect to said conveyor so that the jaws are open at said starting and ending points, each of said jaws being suspended from above by a pair of links, each link on each jaw cooperating with a mating link on the other jaw in a scissor-like arrangement, said means for moving the jaws open including a cam, a head on the lower end of said conduit for sealing contact with the open end of a container to be tested and for introducing a liquid under pressure from said conduit into a container to be tested only while the container is supported from above by said jaws, and a supply conduit connected to said pressure conduit for introducing the liquid under pressure thereinto while the container to be tested is supported by said jaws from above.

9. Apparatus in accordance with claim 8 including a selectively operable means for applying a downwardly directed force on said pressure conduit when a liquid is being introduced into a container by said pressure conduit, thereby opposing any upward reaction force from the pressurized liquid.

10. Apparatus in accordance with claim 9 wherein said jaws are supported by the lower end portion of an upright member, said selectively operable means including a member pivoted to the upper end of said upright member.

* * * * *